United States Patent
Manneck et al.

(10) Patent No.: US 9,993,406 B2
(45) Date of Patent: *Jun. 12, 2018

(54) AGENT AND METHOD FOR OXIDATIVE HAIR COLORING WHICH ARE GENTLE ON KERATIN FIBERS

(71) Applicant: Henkel AG & Co. KGaA, Duesseldorf (DE)

(72) Inventors: Hartmut Manneck, Barnitz (DE); Thomas Hippe, Appen (DE); Stefan Hoepfner, Hamburg (DE); Jessica Brender, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/410,315

(22) Filed: Jan. 19, 2017

(65) Prior Publication Data

US 2017/0202763 A1 Jul. 20, 2017

Related U.S. Application Data

(60) Provisional application No. 62/345,088, filed on Jun. 3, 2016.

(30) Foreign Application Priority Data

Jan. 20, 2016 (DE) .......................... 10 2016 200 688

(51) Int. Cl.
| | |
|---|---|
| *A61Q 5/10* | (2006.01) |
| *A61K 8/44* | (2006.01) |
| *A61K 8/22* | (2006.01) |
| *A61K 8/362* | (2006.01) |
| *A61K 8/81* | (2006.01) |
| *A61K 8/41* | (2006.01) |
| *A61K 8/34* | (2006.01) |
| *A61K 8/49* | (2006.01) |

(52) U.S. Cl.
CPC .................. *A61K 8/44* (2013.01); *A61K 8/22* (2013.01); *A61K 8/347* (2013.01); *A61K 8/362* (2013.01); *A61K 8/41* (2013.01); *A61K 8/415* (2013.01); *A61K 8/447* (2013.01); *A61K 8/4926* (2013.01); *A61K 8/817* (2013.01); *A61K 8/8129* (2013.01); *A61Q 5/10* (2013.01); *A61K 2800/4324* (2013.01); *A61K 2800/882* (2013.01)

(58) Field of Classification Search
CPC . A61K 8/44; A61K 8/22; A61K 8/362; A61K 8/447; A61K 8/817; A61K 8/8129; A61K 8/415; A61K 2800/4324; A61K 2800/882; A61Q 5/10
See application file for complete search history.

(56) References Cited

U.S. PATENT DOCUMENTS

| | | | | |
|---|---|---|---|---|
| 2002/0189034 A1 * | 12/2002 | Kitabata | .................. | A61K 8/19 8/405 |
| 2008/0141468 A1 | 6/2008 | Cotteret | | |
| 2008/0262085 A1 | 10/2008 | Kainz et al. | | |
| 2015/0053228 A1 * | 2/2015 | Bonauer | ............ | A45D 19/0008 132/208 |

FOREIGN PATENT DOCUMENTS

| | | |
|---|---|---|
| DE | 10051774 A1 | 4/2002 |
| EP | 1174112 A2 | 1/2002 |
| KR | 2003-0003970 A | 1/2003 |
| WO | 01/47486 A1 | 7/2001 |
| WO | 02/32383 A2 | 4/2002 |
| WO | 2010/072514 A2 | 7/2010 |

OTHER PUBLICATIONS

STIC Search Report dated Mar. 30, 2017.*
English abstract (May 22, 2017) of the Japanese Patent No. 2006273782 A.*
English transaltion (May 22, 2017) of the Abstract of the Japanese Patent No. JP2006273782 A.*
PCT International Search Report (PCT/EP2016/079378) dated Dec. 22, 2016.
Database Chemical Abstracts Service, "Hair Dye Compositions Containing Glycolic Acids and Polycarboxylic Acids", XP002765493, Database Accession No. 132:313323, 2000.
Database Chemical Abstracts Service, "Antioxidants and Hydroxy Radical Inhibitors Containing Bunte Salts", XP002765495, Database Accession No. 138:373793, 2003.
Database Chemical Abstracts Service, "Hair Processing Agent Kits Containing Dialkyl Phosphates, Nonionic Surfactants, and Polyhydric Alcohols", XP002765494, Database Accession No. 149:61534, 2008.

* cited by examiner

Primary Examiner — Eisa B Elhilo
(74) Attorney, Agent, or Firm — James J. Cummings

(57) ABSTRACT

Coloring agents for keratin fibers, in particular for human hair, include—based on their weight—at least one compound selected from the group of oxidation dye precursors, substantive dyes and mixtures thereof, 0.1 to 5% by weight dicarboxylic acid(s) having 2 to 10 carbon atoms and/or salt(s) of said acid(s), 20 to 95% by weight water and less than 0.1% by weight peroxide compound(s), result in oxidative coloring agents with improved fiber protection.

10 Claims, No Drawings

AGENT AND METHOD FOR OXIDATIVE HAIR COLORING WHICH ARE GENTLE ON KERATIN FIBERS

FIELD OF THE INVENTION

The present invention generally relates to an agent for oxidative hair coloring which is gentle on the hair, and to a gentle method for oxidative hair coloring, in which keratin fibers are protected against oxidative effects and/or oxidative hair damage is repaired.

BACKGROUND OF THE INVENTION

During the oxidative coloring of hair, damage to the keratin fibers may occur due to the aggressive agents. In particular, the natural hydrophobicity of the keratin fibers is reduced since the coloring agents must first make the hair penetrable in order to take effect. On the one hand, however, the water-repelling effect is a natural mode of protection for the hair, and on the other hand parameters desired by the consumer, such as shine, suppleness, feel and "fall" of the hair, are closely linked thereto.

In order to overcome the aforementioned disadvantages, so-called pretreatment agents are available on the market, which are said to protect the hair against the aggressive effect. However, said pretreatment agents often weigh down the hair or adversely affect the outcome of the subsequent lightening or coloring of the hair. In particular, the wash fastness of the coloring may be worsened by the pretreatment agent. Also known are numerous aftertreatment agents which attempt to repair the damage to the hair that is caused during the oxidative coloring treatment. However, all of these methods require a multistage application process, specifically the need to apply a further hair treatment agent either before or after the coloring operation. This is often perceived as bothersome by the consumer, since already the oxidative coloring treatment itself, which involves multiple operating steps and a leave-in time of up to 60 minutes, is very time-consuming.

It is therefore desirable to provide an agent and a method for oxidative hair coloring by way of a hair-protecting treatment, which overcomes the aforementioned disadvantages without having a negative effect on the color result of the oxidative coloring treatment. In particular, it is desirable to provide a coloring agent and a method by which the hair is not weighed down and as little damage to the hair as possible occurs. It is also desirable for the hair protection achieved to take as little time as possible and to take place as far as possible together with the coloring step itself.

The use of dicarboxylic acids such as succinic acid in hair care is prior art. These are widely used in shampoos and particularly in conditioners, in order to provide a caring effect. For instance, patent application WO 2005/115314 A1 discloses a method for restructuring keratin fibers, in which the keratin fibers are brought into contact with cystine and with at least one dicarboxylic acid having 2 to 10 carbon atoms, wherein preferred dicarboxylic acids are selected from oxalic acid, malonic acid, succinic acid, glutaric acid, adipic acid, pimelic acid, azelaic acid, maleic acid, fumaric acid and sorbic acid, and particular preference is given to succinic acid. Patent application DE 10051774 A1 describes the use of short-chain carboxylic acids having a molecular weight of less than 750 g/mol in cosmetic agents as an active substance for restructuring keratin fibers. Patent application EP 1174112 A discloses hair treatment agents which, besides an organic acid, include as further mandatory constituents an organic solvent, a cationic surfactant and a higher alcohol, and serve for repairing pores in hair.

More recently, agents which are intended to be mixed with coloring compositions for the purpose of protecting fibers and which include dicarboxylic acids have also been offered on the market. With such agents, admittedly no additional hair treatment agent is applied before or after the coloring operation, but the agent must still be mixed with the actual coloring agent prior to application, which likewise means a further operating step and is perceived as bothersome by the consumer.

In view of the above, desirable features and characteristics of the present invention will become apparent from the subsequent detailed description of the invention and the appended claims.

BRIEF SUMMARY OF THE INVENTION

A coloring agent for keratin fibers, in particular for human hair, containing—based on its weight—at least one compound selected from the group of oxidation dye precursors, substantive dyes and mixtures thereof, 0.1 to 5% by weight dicarboxylic acid(s) having 2 to 10 carbon atoms and/or salt(s) of said acid(s); 20 to 95% by weight water; and less than 0.1% by weight peroxide compound(s).

A method for the oxidative coloring of keratin fibers, in particular human hair, includes the following method steps I. providing a) at least one compound selected from the group of oxidation dye precursors, substantive dyes and mixtures thereof, b) 0.1 to 5% by weight dicarboxylic acid(s) having 2 to 10 carbon atoms and/or salt(s) of said acid(s), c) 20 to 95% by weight water, and d) less than 0.1% by weight peroxide compound(s); II. providing a composition (B) containing at least one peroxide compound which is preferably hydrogen peroxide, wherein the composition (B) preferably has a pH in the range of 2.5 to 6.5, preferably 3.0 to 5.5, particularly preferably 3.5 to 5.0, in each case measured at 20° C.; III. mixing the compositions (A) and (B) with one another, then immediately; IV. applying the mixture of (A) and (B) to the keratin fibers, in particular to the human hair; V. rinsing out after a leave-in time of 0.1 to 60 minutes, preferably 1 to 45 minutes, particularly preferably 10 to 30 minutes; and VI. optionally further hair treatments, such as styling, conditioning and/or drying.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that oxidative coloring agents with improved fiber protection can be provided if the color cream that is to be mixed with the developer in the course of preparation by the customer includes, besides typical constituents such as water and dyes or precursors thereof, at least one dicarboxylic acid having 2 to 10 carbon atoms, and is largely free of peroxides. In this case, not only is a further operating step avoided, but these agents, for otherwise identical use amounts of dicarboxylic acid(s), are also more effective at protecting fibers than when added subsequently.

In a first embodiment, the present invention relates to coloring agents for keratin fibers, in particular for human hair, containing—based on their weight— a) at least one compound selected from the group of oxidation dye precursors, substantive dyes and mixtures thereof,
b) 0.1 to 5% by weight dicarboxylic acid(s) having 2 to 10 carbon atoms and/or salt(s) of said acid(s),
c) 20 to 95% by weight water and
d) less than 0.1% by weight peroxide compound(s).

Another subject matter of the present invention is a method for the oxidative coloring of keratin fibers, in particular human hair, which comprises the following method steps I. providing a composition (A), containing—based on its weight—
   a) at least one compound selected from the group of oxidation dye precursors, substantive dyes and mixtures thereof,
   b) 0.1 to 5% by weight dicarboxylic acid(s) having 2 to 10 carbon atoms and/or salt(s) of said acid(s),
   c) 20 to 95% by weight water and
   d) less than 0.1% by weight peroxide compound(s)
II. providing a composition (B) containing at least one peroxide compound which is preferably hydrogen peroxide,
   wherein the composition (B) preferably has a pH in the range of 2.5 to 6.5, preferably 3.0 to 5.5, particularly preferably 3.5 to 5.0, in each case measured at 20° C.
III. mixing the compositions (A) and (B) with one another, then immediately
IV. applying the mixture of (A) and (B) to the keratin fibers, in particular to the human hair, and
V. rinsing out after a leave-in time of 0.1 to 60 minutes, preferably 1 to 45 minutes, particularly preferably 10 to 30 minutes
VI. optionally further hair treatments, such as styling, conditioning and/or drying.

Keratin fibers are to be understood to mean wool, furs, feathers and in particular human hair. However, the coloring agents according to the invention can in principle also be used for coloring other natural fibers, such as for example cotton, jute, sisal, linen or silk, modified natural fibers, such as for example regenerated cellulose, nitrocellulose, alkyl cellulose or hydroxyalkyl cellulose or acetyl cellulose.

The agents according to the invention or used in the method according to the invention preferably include at least one coupler component. Particularly gentle colorations can be achieved if the agents include as the coupler component at least one coupler component selected from the group formed of 3-amino-2-methylamino-6-methoxypyridine, 3-amino-6-methylphenol, 3-amino-2-hydroxypyridine, 1,3-bis-(2,4-diaminophenoxy)propane, 2, 7-dihydroxynaphthalene, 2-methylresorcinol, 2,5-dimethylresorcinol, 4-chlororesorcinol, 3-aminophenol, 2-amino-3-hydroxypyridine, 2-chloro-6-methyl-3-aminophenol, 2,6-dihydroxy-3,4-dimethylpyridine, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 1-methoxy-2-amino-4-beta-hydroxyethylaminobenzene (Lehmann's Blue), 2,4-diaminophenoxyethanol, 5-amino-4-chloro-o-cresol, 2,4-dichloro-m-aminophenol, 2,6-dihydroxy-3,4-dimethylpyridine and/or a physiologically acceptable salt of said compounds.

Agents which are likewise preferred according to the invention are characterized in that they include the at least one coupler component and/or the physiologically acceptable salt thereof in a proportion by weight of 0.001 to 5.0% by weight, more preferably 0.025 to 2.5% by weight, particularly preferably 0.05 to 2% by weight and in particular 0.1 to 1.5% by weight, in each case based on the total weight of the ready-to-use agent.

In order to achieve a balanced and subtle development of shades, it is advantageous according to the invention if further color-imparting components are included in the agent according to the invention.

It may therefore be preferred according to the invention if the agent according to the invention or used in the method according to the invention includes at least one further color-imparting component which is selected from additional oxidation dye precursors of the developer type and/or substantive dyes.

Preferred further developer components are selected from at least one compound from the group formed of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-2-propanol, bis-(2-hydroxy-5-aminophenyl)methane, 1,3-bis-(2, 5-diaminophenoxy)-2-propanol, N,N'-bis-(4-aminophenyl)-1,4-diazacycloheptane, 1,10-bis-(2, 5-diaminophenyl)-1,4,7,10-tetraoxadecane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4, 5-diamino-1-(2-hydroxyethyl)pyrazole, 2,4,5,6-tetraaminopyrimidine, 4-hydroxy-2, 5,6-triaminopyrimidine, 2-hydroxy-4,5,6-triaminopyrimidine, as well as the physiologically acceptable salts of said compounds. Particularly preferred additional developer components in this regard are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine and/or 4,5-diamino-1-(2-hydroxyethyl)pyrazole, as well as the physiologically acceptable salts thereof.

The developer components are preferably used in an amount of 0.0001 to 10% by weight, preferably 0.001 to 5% by weight, in each case based on the ready-to-use agent.

To sum up, preference is given to coloring agents according to the invention or used in the method according to the invention which include 0.05 to 5% by weight, preferably 0.1 to 4.5% by weight, more preferably 0.15 to 4% by weight, even more preferably 0.2 to 3.5% by weight and in particular 0.25 to 3% by weight oxidation dye precursors.

Instead of oxidation dye precursors or in addition thereto, the agents according to the invention or used in the method according to the invention may include at least one substantive dye. These are dyes which are directly absorbed onto the hair and do not require any oxidative process to develop the color. Substantive dyes are usually nitrophenylenediamines, nitroaminophenols, azo dyes, anthraquinones or indophenols.

The substantive dyes are in each case used preferably in an amount of 0.001 to 20% by weight, in particular 0.05 to 5% by weight, in each case based on the total ready-to-use preparation. The total amount of substantive dyes is preferably at most 3% by weight.

Substantive dyes can be subdivided into anionic, cationic and nonionic substantive dyes, which are selected and used by the person skilled in the art based on the requirements of the carrier.

Preferred anionic substantive dyes are the compounds known under the international designations or trade names Bromophenol Blue, Tetrabromophenol Blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic substantive dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), Basic Blue 99, Basic Brown 16 and Basic Brown 17 as well as Yellow 87, Basic Orange 31 and Basic Red 51.

Nonionic nitro and quinone dyes and neutral azo dyes are particularly suitable as nonionic substantive dyes. Preferred nonionic substantive dyes are the compounds known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl) amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

The agents according to the invention or used in the method according to the invention may also include nature-analogous dyes. Compositions according to the invention which include precursors of nature-analogous dyes are preferably used as air-oxidative coloring agents. In this embodiment, therefore, no additional oxidizing agent is added to said compositions prior to use.

The dye precursors of nature-analogous dyes are in each case used preferably in an amount of 0.001 to 5% by weight, based on the total ready-to-use preparation. Particularly suitable precursors of nature-analogous hair dyes are derivatives of 5,6-dihydroxyindoline, in particular 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline as well as 5,6-dihydroxyindoline-2-carboxylic acid, as well as other derivatives of 5,6-dihydroxyindole, in particular 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, as well as physiologically acceptable salts of the aforementioned compounds.

To sum up, preference is given to coloring agents according to the invention or used in the method according to the invention which include 0.05 to 5% by weight, preferably 0.1 to 4.5% by weight, more preferably 0.15 to 4% by weight, even more preferably 0.2 to 3.5% by weight and in particular 0.25 to 3% by weight substantive dye(s).

The agents according to the invention or used in the method according to the invention include 0.1 to 5% by weight dicarboxylic acid(s) having 2 to 10 carbon atoms and/or salt(s) of said acid(s).

Dicarboxylic acids having 2 to 10 carbon atoms which are preferred according to the invention are selected from succinic acid, oxalic acid, malonic acid, adipic acid, pimelic acid, suberic acid, azelaic acid, sebacic acid, maleic acid, fumaric acid and mixtures of said acids. Succinic acid and/or maleic acid are particularly preferred according to the invention. Said dicarboxylic acids significantly help to reduce the damage to the hair that is brought about by the coloring agents according to the invention.

Depending on the pH of the coloring agent according to the invention or of the compositions used in one of the coloring methods according to the invention, the at least one dicarboxylic acid having 2 to 10 carbon atoms may be in the form of an undissociated acid or in partially dissociated or completely dissociated form. If the at least one dicarboxylic acid having 2 to 10 carbon atoms is in partially dissociated or completely dissociated form, the counter-ion is selected from physiologically acceptable cations, such as in particular the alkali metal, alkaline earth metal and zinc ions as well as ammonium ions, alkylammonium ions, alkanolammonium ions and glucammonium ions, in particular the mono-, di- and trimethyl-, -ethyl- and -hydroxyethyl ammonium ions. Preference is also given to the salts of the saturated dicarboxylic acids having 2 to 10 carbon atoms with amino-$C_1$-$C_6$-alkanols, in particular with monoethanolamine, and amino-$C_1$-$C_6$-alkanediols, in particular with 2-amino-2-methyl-1-propanol, 2-amino-2-methyl-1,3-propanediol, 2-amino-1-propanol, 3-amino-1-propanol, 1-amino-2-propanol (MIPA) and 2-amino-2-(hydroxymethyl)-1,3-propanediol (TRIS), particular preference being given to the salts with monoethanolamine, 2-amino-2-methyl-1-propanol and 2-amino-2-methyl-1,3-propanediol.

Sodium, potassium, magnesium, ammonium and monoethanol ammonium ions are extremely preferred as counter-ions for the partially or completely dissociated dicarboxylic acids having 2 to 10 carbon atoms. Besides these, however, use may also be made of dicarboxylic acids which have 2 to 10 carbon atoms and which are neutralized with alkaline-reacting amino acids, such as for example arginine, lysine, ornithine and histidine.

The sodium, potassium, ammonium, monoethanol ammonium, lysine and arginine salts and mixtures thereof are preferred salts of the dicarboxylic acids having 2 to 10 carbon atoms.

Preferred coloring agents according to the invention include the at least one dicarboxylic acid having 2 to 10 carbon atoms or one or more salts thereof in a total amount of 0.2 to 4% by weight, preferably 0.33 to 3% by weight, particularly preferably 0.5 to 2% by weight, in each case converted to the undissociated acid and based on the weight of the coloring agent.

Even when the dicarboxylic acids are present in salt form, the amounts specified above relate to the respective dicarboxylic acid in undissociated form, so as not to falsify the stated amounts due to different molecular weights of the salts. For example, an initial sample weight of 15% by weight disodium succinate hexahydrate would give, when converted, a succinic acid concentration of 6.55% by weight.

To sum up, preference is given to coloring agents according to the invention or used in the method according to the invention in which the at least one dicarboxylic acid having 2 to 10 carbon atoms is selected from succinic acid, oxalic acid, malonic acid, adipic acid, pimelic acid, suberic acid, azelaic acid, sebacic acid, maleic acid, fumaric acid and mixtures of said acids, preferably selected from succinic acid and/or maleic acid.

Particular preference is given to coloring agents according to the invention or used in the method according to the invention which include at least one dicarboxylic acid having 2 to 10 carbon atoms in a total amount of 0.2 to 4% by weight, preferably 0.33 to 3% by weight, particularly preferably 0.5 to 2% by weight, in each case converted to the undissociated acid and based on the weight of the coloring agent.

Very particularly preferred coloring agents according to the invention or used in the method according to the invention include 0.2 to 4% by weight, preferably 0.33 to 3% by weight, particularly preferably 0.5 to 2% by weight succinic acid, in each case converted to the undissociated acid and based on the weight of the coloring agent.

Extremely preferred coloring agents according to the invention or used in the method according to the invention include 0.2 to 4% by weight, preferably 0.33 to 3% by weight, particularly preferably 0.5 to 2% by weight maleic acid, in each case converted to the undissociated acid and based on the weight of the coloring agent.

The coloring agents according to the invention or used in the method according to the invention include 20 to 95% by weight water. Preferred agents include 30 to 90% by weight, particularly preferably 40 to 85% by weight, extremely preferably 45 to 82.5% by weight and in particular 40 to 80% by weight water, in each case based on the total weight of the coloring agent according to the invention.

The coloring agents according to the invention or used in the method according to the invention include less than 0.1% by weight peroxide compound(s). Surprisingly, given otherwise equal use amounts, hair dyes produced from agents according to the invention by adding oxidizing agent preparations ("developers") are more effective at protecting fibers than those obtained from conventional color creams, developers and a subsequent admixing of dicarboxylic acid(s).

It is preferred to have an even lower peroxide content in the coloring agents according to the invention or used in the method according to the invention. Particularly preferred coloring agents according to the invention or used in the method according to the invention include less than 0.01% by weight, preferably less than 0.005, particularly preferably less than 0.001% by weight peroxide compounds and are in particular free of peroxide compounds.

Particularly preferred coloring agents according to the invention or used in the method according to the invention include less than 0.01% by weight, preferably less than 0.005, particularly preferably less than 0.001% by weight hydrogen peroxide (calculated as 100% strength $H_2O_2$). Very particularly preferred agents are completely free of hydrogen peroxide.

Particularly preferred coloring agents according to the invention or used in the method according to the invention include less than 0.01% by weight, preferably less than 0.005, particularly preferably less than 0.001% by weight potassium, sodium and/or ammonium persulfate. Very particularly preferred agents are completely free of persulfates.

The coloring agents according to the invention or used in the method according to the invention preferably include at least one amino acid of formula (I)

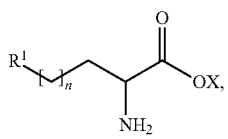

(I)

in which
X represents a hydrogen atom or a monovalent or divalent cation;
n represents zero, 1, 2 or 3;
$R^1$ represents a radical selected from an amino group, a guanidine group, a (1H-imidazol-4-yl) group, a carboxamide group —$CONH_2$, a 1H-indol-3-yl group, a thiol group —SH and a methylsulfanyl group —$SCH_3$, or at least one salt of said amino acid.

Said amino acids give the coloring agents according to the invention or used in the method according to the invention a further improved fiber-protecting effect.

Preferred amino acids of formula (I) are selected from arginine, lysine, histidine, asparagine, glutamine, cysteine, methionine, tryptophan and mixtures thereof. Particularly preferred coloring agents include mixtures of arginine and lysine or at least one salt of said amino acids.

Preferred coloring agents according to the invention include the at least one amino acid of formula (VI) or one or more salts thereof in a total amount of 0.05 to 3% by weight, preferably 0.1 to 2% by weight, particularly preferably 0.2 to 1.2% by weight, in each case converted to the undissociated acid and based on the weight of the coloring agent. Further particularly preferred coloring agents according to the invention include mixtures of arginine and lysine or at least one salt of said amino acids in a total amount of 0.05 to 3% by weight, preferably 0.1 to 2% by weight, particularly preferably 0.2 to 1.2% by weight, in each case converted to the undissociated acid and based on the weight of the coloring agent.

Extremely preferred coloring agents according to the invention or used in the method according to the invention additionally include at least one amino acid from the group arginine, lysine, histidine, asparagine, glutamine, cysteine, methionine, tryptophan and mixtures thereof, particularly preferably mixtures of arginine and lysine, in a total amount of 0.05 to 3% by weight, preferably 0.1 to 2% by weight, particularly preferably 0.2 to 1.2% by weight, in each case converted to the undissociated acid and based on the weight of the coloring agent.

It has also surprisingly been found that the reduced hair-damaging effect of the coloring agents according to the invention or used in the method according to the invention can be further supported if at least one compound of general formula (II) is included therein.

Therefore, preferred coloring agents according to the invention or used in the method according to the invention additionally include at least one compound of general formula (II)

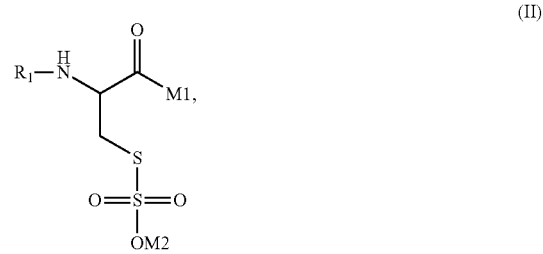

(II)

wherein
R1 represents a hydrogen atom or a structural element of formula (IV)

(IV)

wherein
x represents an integer from 1 to 100,
the radical R2 in each of the structural elements of formula (IV) can in each case be selected independently of the preceding structural element of formula (IV), R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 represents the group —OM2 or a structural element of formula (V)

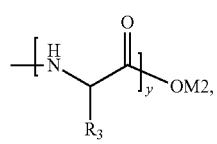

(V)

wherein
y represents an integer from 1 to 100,
the radical R3 in each of the structural elements of formula (V) can in each case be selected independently of the preceding structural element of formula (V),
R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M2 represents a hydrogen atom, an equivalent of a monovalent or polyvalent cation or an ammonium ion $(NH_4)^+$,
wherein preferably one or more compounds of the above formula (II) are included in a total amount of 0.001 to 2.5% by weight, more preferably 0.01 to 1.0% by weight and particularly preferably 0.02 to 0.1% by weight, in each case based on the weight of the coloring agent according to the invention.

The compounds of formula (II) to be optionally used are the Bunte salt of an amino acid, oligopeptide or peptide.

The radical R1 may represent either a hydrogen atom or a structural element of formula (IV)

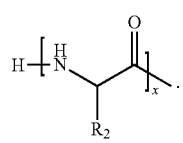

(IV)

The structural element of formula (IV) is also characterized by the repeat index x, where x represents an integer from 1 to 100. The repeat index x indicates how many structural elements of formula (IV) are included in the compound of formula (II).

Preferably, x represents an integer from 1 to 50. More preferably, x represents an integer from 1 to 20. With very particular preference, x represents an integer from 1 to 10.

If x represents for example the number 10, the compound of formula (II) includes 10 structural elements of formula (IV).

It is essential here that the radical R2 in each of the structural elements of formula (IV) can in each case be selected independently of the preceding structural element of formula (IV). If, for example, the compounds of formula (II) include 10 structural units of formula (IV), then these 10 structural units may be identical or different.

The radical R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group.

The structural element of formula (IV) is thus an amino acid which is peptide-linked via its amino and/or acid function within the compound of formula (II). If the amino acid is cysteine, this may also be in the form of a Bunte salt.

If the radical R2 represents a hydrogen atom, the structural element of formula (IV) is based on the amino acid glycine. If R2 is a methyl group, the structural element of formula (IV) is based on the amino acid alanine.

Analogously:

| If the radical R2 represents | the structural element of formula (IV) is based on the amino acid |
|---|---|
| $(H_3C)_2CH—$ | Valine |
| $(H_3C)_2CH—CH_2—$ | Leucine |
| $H_3C—CH_2—CH(CH_3)—$ | Isoleucine |
| $C_6H_5—CH_2—$ | phenylalanine |
| $4\text{-}OH—C_6H_5—CH_2—$ | Tyrosine |
| $HO—CH_2—$ | Serine |
| $H_3C—CH(OH)—$ | Threonine |
| $H_2N—CH_2—CH_2—CH_2—CH_2—$ | Lysine |
| $H_2N—C(NH)—NH—CH_2—CH_2—CH_2—$ | Arginine |
| $HOOC—CH_2—CH_2—$ | glutamic acid |
| $HOOC—CH_2—$ | aspartic acid |
| $H_2N—C(O)—CH_2—CH_2—$ | Glutamine |
| $H_2N—C(O)—CH_2—$ | Asparagine |
| $HS—CH_2—$ | Cysteine |
| $H_3C—S—CH_2—CH_2—$ | methionine |
| 1H-imidazol-4-ylmethyl- | Histidine |
| 1H-indol-3-ylmethyl- | tryptophan |

Finally, the radical R2 may also represent a (sulfosulfanyl)methyl group. This is a Bunte salt structure of formula $HO—S(O_2)—S—CH_2—$.

Depending on the pH of the coloring agent, the Bunte salt structure of formula $HO—S(O_2)—S—CH_2—$ may also be in its deprotonated form.

Within the compound of formula (II), M1 represents the group —OM2 or a structural element of formula (V)

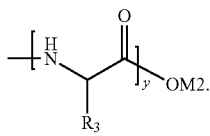

The structural element of formula (V) is characterized by the repeat index y, where y represents an integer from 1 to 100. The repeat index y indicates how many structural elements of formula (V) are included in the compound of formula (II).

Preferably, y represents an integer from 1 to 50. More preferably, y represents an integer from 1 to 20. With very particular preference, y represents an integer from 1 to 10.

If y represents for example the number 10, the compound of formula (II) includes 10 structural elements of formula (V).

It is essential here that the radical R3 in each of the structural elements of formula (V) can in each case be selected independently of the preceding structural element of formula (V). If, for example, the compounds of formula (II) include 10 structural units of formula (V), then these 10 structural units may be identical or different.

The radical R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group.

The structural element of formula (V) is thus also an amino acid which is peptide-linked via its amino and/or acid function within the compound of formula (II). If the amino acid is cysteine, this may also be in the form of a Bunte salt.

| If the radical R3 represents | the structural element of formula (V) is based on the amino acid |
|---|---|
| —H | Glycine |
| —CH$_3$ | Alanine |
| (H$_3$C)$_2$CH— | Valine |
| (H$_3$C)$_2$CH—CH$_2$— | Leucine |
| H$_3$C—CH$_2$—CH(CH$_3$)— | isoleucine |
| C$_6$H$_5$—CH$_2$— | phenylalanine |
| 4-OH—C$_6$H$_5$—CH$_2$— | Tyrosine |
| HO—CH$_2$— | Serine |
| H$_3$C—CH(OH)— | threonine |
| H$_2$N—CH$_2$—CH$_2$—CH$_2$—CH$_2$— | Lysine |
| H$_2$N—C(NH)—NH—CH$_2$—CH$_2$—CH$_2$— | Arginine |
| HOOC—CH$_2$—CH$_2$— | glutamic acid |
| HOOC—CH$_2$— | aspartic acid |
| H$_2$N—C(O)—CH$_2$—CH$_2$— | glutamine |
| H$_2$N—C(O)—CH$_2$— | asparagine |
| HS—CH$_2$— | Cysteine |
| H$_3$C—S—CH$_2$—CH$_2$— | methionine |
| 1H-imidazol-4-ylmethyl- | Histidine |
| 1H-indol-3-ylmethyl- | tryptophan |

Finally, the radical R3 may also represent a (sulfosulfanyl)methyl group. This is a Bunte salt structure of formula HO—S(O$_2$)—S—CH$_2$—.

Here, too, depending on the pH of the coloring agent, the Bunte salt structure of formula HO—S(O$_2$)—S—CH$_2$— may also be in its deprotonated form.

The radical M2 represents a hydrogen atom, an equivalent of a monovalent or polyvalent cation or an ammonium ion (NH$_4$)$^+$.

As preferred equivalents of a monovalent or polyvalent cation, mention may be made in particular of the cations of sodium and potassium (Na$^+$ and K$^+$) or also magnesium or calcium (½Mg$^{2+}$ or ½Ca$^{2+}$).

If M2 represents a hydrogen atom, then the group —OM2 is the group —OH. If M2 represents a sodium cation, then the group —OM2 is the group —ONa. If M2 represents a potassium cation, then the group —OM2 is the group —OK. If M2 represents an ammonium ion, then the group —OM2 is the group —O(NH$_4$).

The group —OM2 is always adjacent to a carbonyl group. To sum up, when M2 represents H, K, Na or ammonium, it therefore exists in the compound of formula (II) either in the form of an acid in its protonated form or else the sodium, potassium or ammonium salt of said acid.

The compounds of formula (II) according to the invention are either the Bunte salt of the amino acid cysteine, the Bunte salts of oligopeptides, or the Bunte salts of peptides.

If the radical R1 represents a hydrogen atom and the radical M1 represents a group —OM2, then the compound of formula (II) is the Bunte salt of the amino acid cysteine. In this case, the compound of formula (II) is the compound of formula (IIa)

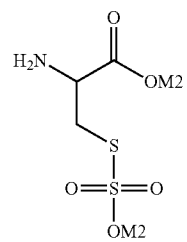

(IIa)

wherein M2 is again defined as described above.

If the compound of formula (IIa) is in the form of its free acid, it is 2-amino-3-(sulfosulfanyl)propanoic acid. This substance is commercially available.

It has been found that the use of the compound of formula (IIa) in coloring agents, even in particularly small use amounts, leads to a particularly effective reduction in damage to the hair, said reduction still persisting even after repeated washing of the hair. The use of compounds of formula (IIa) is therefore very particularly preferred.

In one very particularly preferred embodiment, a coloring agent according to the invention or used in the method according to the invention is characterized in that it includes at least one compound of formula (II), wherein
R1 represents a hydrogen atom and
M1 represents a group —OM2.

If a compound of formula (IIa) is used, preferably said specific compound is used. If, however, the Bunte salts of oligopeptides are used as compounds of formula (II), then the coloring agent according to the invention may also include multiple compounds of formula (II) as a mixture of different oligopeptides. These oligopeptides are defined by their average molecular weight. The average molecular weight $M_w$ of the at least one oligopeptide of formula (II) can be determined for example by gel permeation-chromatography (GPC) using polystyrene as the internal standard.

Depending on how many structural elements of formula (IV) and/or (V) are included in the compound of formula (II), and depending on the type of said amino acids, the molecular weight of the compound of formula (II) used according to the invention may vary. It is particularly preferred according to the invention if the compound of formula (II) is an oligopeptide which has a molecular weight $M_w$ of 200 to 2000 Da, preferably 250 to 1500 Da, preferably 300 to 1200 Da, in particular 400 to 800 Da.

In the context of the present invention, the term "oligopeptide" will be understood to mean condensation products of amino acids which have the molecular weights specified above.

In one very particularly preferred embodiment, a coloring agent according to the invention is characterized in that it includes at least one compound of formula (II) which has a molecular weight $M_w$ of 200 to 2000 Da (Dalton), preferably 250 to 1500 Da, preferably 300 to 1200 Da, in particular 400 to 800 Da.

If a mixture of oligomers is used in the coloring agent according to the invention, these mixtures can be defined by their average molecular weight.

In this case, a preferred coloring agent according to the invention is characterized in that it includes at least one mixture of compounds of formula (II) which has an average molecular weight $M_w$ of 200 to 2000 Da, preferably 250 to 1500 Da, preferably 300 to 1200 Da, in particular 400 to 800 Da.

It has also been found that the protective effect or repair effect exhibited by the compounds of formula (II) also depends on the repeat indices x and y. As described above, it is very particularly preferred if x represents an integer from 1 to 10 and y represents an integer from 1 to 10.

In another very particularly preferred embodiment, a coloring or bleaching agent according to the invention is characterized in that it includes at least one compound of formula (II), wherein
R1 represents a structural element of formula (IV), and
M1 represents a structural element of formula (V), and
x represents an integer from 1 to 10 and
y represents an integer from 1 to 10.

Besides the molecular weight of the compound of formula (II), the amount of Bunte salt units included in the compound of formula (II) also has a critical influence on the efficacy of the protective effect or "repair effect" of the compounds.

Compounds having at least one Bunte salt unit—as is present for example in the compound of formula (IIa)—are very effective, particularly when they are used as a monomeric compound. Oligopeptides having at least one Bunte salt unit are particularly effective when they have a low molecular weight of up to 1200, in particular 800 Dalton.

When using oligopeptides, however, it is of very particular advantage if the compound of formula (II) has at least two, preferably at least three Bunte salt units.

In another very particularly preferred embodiment, a coloring agent according to the invention is characterized in that it includes at least one compound of formula (II), wherein
R1 represents a structural element of formula (IV), and
the radical R2 in at least one structural element of formula (IV) represents a (sulfosulfanyl)methyl group (that is to say a group HO—S(O$_2$)—S—CH$_2$—).

In another very particularly preferred embodiment, a coloring agent according to the invention is characterized in that it includes at least one compound of formula (II), wherein
R1 represents a structural element of formula (IV), and
x represents an integer of at least 3 and
the radical R2 in at least 3 structural elements of formula (IV) represents a 2-carboxyethyl group (that is to say a group HOOC—CH2-CH2-).

In another very particularly preferred embodiment, a coloring agent according to the invention is characterized in that it includes at least one compound of formula (II), wherein
M1 represents a structural element of formula (V), and
y represents an integer of at least 3 and
the radical R3 in at least 3 structural elements of formula (IV) represents a group (Glu).

The at least one compound of formula (II) is included in a total amount of 0.001 to 10% by weight, based on the total weight of the coloring agent preferred according to the invention.

However, it has surprisingly been found that the compound(s) of formula (II) can bring about a very good reduction in damage to the hair even when used in low concentrations. For this reason, it is particularly advantageous if the coloring agent preferred according to the invention includes one or more compounds of the above formula (II) in a total amount of 0.001 to 2.5% by weight, more preferably 0.01 to 1.0% by weight and particularly preferably 0.02 to 0.1% by weight, in each case based on the weight of the coloring agent according to the invention.

In another very particularly preferred embodiment, a coloring agent according to the invention is characterized in that it includes one or more compounds of the above formula (II) in a total amount of 0.001 to 2.5% by weight, more preferably 0.01 to 1.0% by weight and particularly preferably 0.02 to 0.1% by weight, in each case based on the weight of the coloring agent according to the invention.

It has also surprisingly been found that the effect of reduced hair damage brought about by the coloring agents according to the invention or used in the method according to the invention can be further supported if particular polymers are included therein.

Therefore, preferred coloring agents according to the invention or used in the method according to the invention additionally include at least one polymer A which has at least ten constituent units of formula (I)

in which
X represents nitrogen or oxygen and
$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group, and
p=0 when X represents oxygen and p=1 when X represents nitrogen,
the polymer A containing no permanently ionic constituent units,
wherein the at least one polymer A having at least ten constituent units of formula (I) is preferably included in a total amount of 0.2 to 5% by weight, particularly preferably 0.5 to 3% by weight, extremely preferably 1.0 to 2.3% by weight, in each case based on the weight of the coloring agent.

In the context of the present invention, "polymer" will be understood to mean polymers as per the IUPAC definition, which comprise at least 10 identical constituent units.

The number of constituent units in a polymer is referred to as the degree of polymerization. Polymers A which are preferred according to the invention each have a degree of polymerization in the range from 40 to 1000, preferably 100 to 800, particularly preferably 350 to 650. Other polymers A having at least ten constituent units of formula (I) which are preferred according to the invention include 40 to 1000, preferably 100 to 800, particularly preferably 350 to 650 identical constituent units of formula (I).

$R^1$ and $R^2$ preferably each independently of one another represent hydrogen or a $C_2$-$C_{10}$ acyl group which is preferably selected from an acetyl, propanoyl or n-butanoyl group, particularly preferably selected from an acetyl group.

Polymers A which are preferred according to the invention have at least 10 constituent units of formula (I), in which X represents nitrogen, the polymer A containing no permanently ionic constituent units.

Other polymers A which are particularly preferred according to the invention have at least 10 constituent units of formula (I), in which X represents nitrogen and $R^1$ and $R^2$ together with X form a five-membered or six-membered, saturated or unsaturated ring which optionally includes further heteroatoms preferably selected from N and O, and/or is optionally substituted with at least one C1-C6 alkyl group and/or with at least one functional group.

If $R^1$ and $R^2$ together with X form a five-membered or six-membered, saturated or unsaturated ring which optionally includes further heteroatoms preferably selected from N and O, said ring is preferably substituted with at least one functional group selected from =O. One particularly preferred substituent combination X, $R^1$, $R^2$ is a pyrrolidone group, so that a constituent unit of formula (I) which is particularly preferred according to the invention is a unit of formula (Ia)

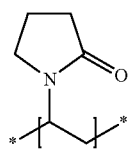

(Ia)

in which X represents nitrogen and $R^1$ and $R^2$ together with said nitrogen atom form a five-membered, saturated ring which includes no further heteroatoms and which is substituted in the 2-position with a functional group =O.

Another particularly preferred substituent combination X, $R^1$, $R^2$ is an ε-caprolactam group, so that a constituent unit of formula (I) which is particularly preferred according to the invention is a unit of formula (Ib)

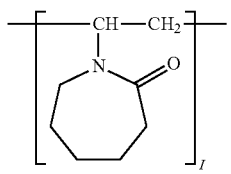

(Ib)

in which X represents nitrogen and $R^1$ and $R^2$ together with said nitrogen atom form a six-membered, saturated ring which includes no further heteroatoms and which is substituted with a functional group =O.

Another particularly preferred substituent combination X, $R^1$, $R^2$ is an imidazole group, so that another unit of formula (I) which is particularly preferred according to the invention is a unit in which X represents nitrogen and $R^1$ and $R^2$ together with said nitrogen atom form a five-membered, unsaturated ring which includes nitrogen as a further heteroatom.

Other polymers A which are preferred according to the invention comprise 25-100 mol %, preferably 55-100 mol %, particularly preferably 85-100 mol % constituent units of formula (I) in which X represents nitrogen, the polymer A containing no permanently ionic constituent units.

Other polymers A which are preferred according to the invention comprise 25-100 mol %, preferably 55-100 mol %, particularly preferably 85-100 mol % constituent units of formula (I) in which X represents nitrogen and $R^1$ and $R^2$ together with X form a five-membered or six-membered, saturated or unsaturated ring which optionally includes further heteroatoms selected from N and O and is optionally substituted with at least one C1-C6 alkyl group and/or with at least one functional group, the polymer A containing no permanently ionic constituent units.

Polymers A which are particularly preferred according to the invention comprise 98-100 mol % constituent units of formula (Ia), the polymer A containing no permanently ionic constituent units.

Polymers A which are extremely preferred according to the invention comprise 98-100 mol % constituent units of formula (Ia) and have a degree of polymerization in the range from 40 to 1000, preferably 100 to 800, particularly preferably 350 to 650, the polymer A containing no permanently ionic constituent units Particularly preferred polymers A are polyvinylpyrrolidone homopolymers having a degree of polymerization in the range from 40 to 1000, preferably 100 to 800, particularly preferably 350 to 650.

Another particularly preferred substituent combination X, $R^1$, $R^2$ is a constituent unit of formula (I) in which X represents oxygen, p is zero and $R^1$ represents hydrogen.

Another particularly preferred substituent combination X, $R^1$, $R^2$ is a constituent unit of formula (I) in which X represents oxygen, p is zero and $R^1$ represents an acetyl group.

Other polymers A which are preferred according to the invention include 75-92 mol % constituent units of formula (I) in which X represents oxygen, p is zero and $R^1$ represents hydrogen, and 8-25 mol % constituent units of formula (I) in which X represents oxygen, p is zero and $R^1$ represents an acetyl group, the polymer A containing no permanently ionic constituent units.

Other polymers A which are preferred according to the invention include 40 to 1000, preferably 100 to 800, particularly preferably 350 to 650 constituent units of formula (I), of which 75-92 mol % constituent units of formula (I) in which X represents oxygen, p is zero and $R^1$ represents hydrogen, and 8-25 mol % constituent units of formula (I) in which X represents oxygen, p is zero and $R^1$ represents an acetyl group, the polymer A containing no permanently ionic constituent units.

Other polymers A which are preferred according to the invention include 65-25 mol % constituent units of formula (Ia) and 35-75 mol % constituent units of formula (I) in which X represents oxygen, p is zero and $R^1$ represents an acetyl group, the polymer A containing no permanently ionic constituent units.

Other polymers A which are preferred according to the invention include 40 to 1000, preferably 100 to 800, particularly preferably 350 to 650 constituent units of formula (I), of which 65-25 mol % constituent units of formula (Ia) and 35-75 mol % constituent units of formula (I) in which X represents oxygen, p is zero and $R^1$ represents an acetyl group, the polymer A containing no permanently ionic constituent units.

The at least one polymer A having at least ten constituent units of formula (I) has no permanently ionic charges. However, it is possible that the constituent units of formula (I) are in ionic form, in particular in cationic form, for example due to protonation of the nitrogen atom in an acidic carrier. However, these charges are not permanent but rather are temporary since they depend on the surrounding medium.

Preferred coloring agents according to the invention include the at least one polymer A having at least ten constituent units of formula (I) in a total amount of 0.2 to 5% by weight, preferably 0.5 to 3% by weight, particularly preferably 1.0 to 2.3% by weight, in each case based on the weight of the coloring agent.

As a further optional ingredient, coloring agents which are preferred according to the invention include at least one permanently cationic polymer B.

Besides at least one permanently cationically charged monomer type, the permanently cationic polymer preferably also includes at least one permanently anionically charged monomer type, the cationic monomers being present in molar excess relative to the anionic monomers so that the at least one second polymer according to the invention has a cationic net charge. Such polymers which are preferred according to the invention are also referred to as amphoteric or zwitterionic polymers.

In a first preferred embodiment, coloring or bleaching agents which are preferred according to the invention include at least one permanently cationic polymer selected from
cationic polymers constructed from monomers with quaternary ammonium groups of general formula (a),

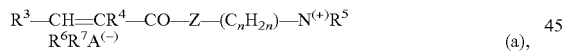

(a), in which $R^3$ and $R^4$ independently of one another represent hydrogen or a methyl group, $R^5$, $R^6$ and $R^7$ independently of one another represent an alkyl group having 1 to 4 carbon atoms, Z represents an NH group or an oxygen atom, n represents an integer from 2 to 4 and $A^{(-)}$ represents the anion of an inorganic or organic acid,
preferably selected from cationic polymers constructed from acrylamidopropyl trimethylammonium chloride,
particularly preferably selected from amphoteric polymers having a cationic net charge which are constructed by polymerization from
a) cationic monomers with quaternary ammonium groups of general formula (a),

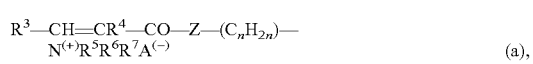

(a), in which $R^3$ and $R^4$ independently of one another represent hydrogen or a methyl group, $R^5$, $R^6$ and $R^7$ independently of one another represent an alkyl group having 1 to 4 carbon atoms, Z represents an NH group or an oxygen atom, n represents an integer from 2 to 4 and $A^{(-)}$ represents the anion of an inorganic or organic acid, and
b) at least one unsaturated carboxylic acid selected from acrylic acid, methacrylic acid and crotonic acid and from mixtures of said acids, wherein the at least one unsaturated carboxylic acid may be in the form of its salts,
wherein in the polymer the cationic monomers are in molar excess relative to the anionic monomers;
extremely preferably selected from amphoteric polymers having a cationic net charge which include the at least one monomer type of general formula (a) and the at least one monomer type of the unsaturated carboxylic acid, selected from acrylic acid, methacrylic acid and crotonic acid and mixtures thereof, in a molar ratio of 60:40 to 95:5, preferably 75:25 to 90:10,
extremely preferably selected from amphoteric copolymers having a cationic net charge which consist of acrylamidopropyl trimethylammonium chloride and acrylic acid in a molar ratio of 60:40 to 95:5, preferably 75:25 to 90:10;
2-[2-hydroxy-3-(trimethylammonio)propoxy]ethyl cellulose ether chloride, which is obtainable for example under the INCI name Polyquaternium-10,
terpolymers of acrylic acid, diallyldimethylammonium chloride and acrylamide, such as those obtainable for example under the INCI name Polyquaternium-39,
homopolymers of N,N,N-trimethyl-2-[(methyl-1-oxo-2-propenyl)oxy]ethanaminium chloride, such as those obtainable for example under the INCI name Polyquaternium-37,
copolymers of diallyldimethylammonium chloride and acrylic acid, such as those obtainable for example under the INCI name Polyquaternium-22,
hydroxyethyl cellulose/dimethyldiallylammonium chloride copolymers, such as those obtainable for example under the INCI name Polyquaternium-4,
copolymers of acrylamide and beta-methacrylyloxyethyl-trimethyl ammonium methosulfate, such as those obtainable for example under the INCI name Polyquaternium-5,
homopolymers of N,N-dimethyl-N-2-propenyl-2-propen-1-aminium chloride, such as those obtainable for example under the INCI name Polyquaternium-6,
copolymers of diallyldimethylammonium chloride and acrylamide, such as those obtainable for example under the INCI name Polyquaternium-7,
copolymers of vinylpyrrolidone and dimethylaminoethyl methacrylate diethyl sulfate, such as those obtainable for example under the INCI name Polyquaternium-11,
and mixtures of the aforementioned polymers.

Permanent cationic polymers which are extremely preferred according to the invention are selected from 2-[2-hydroxy-3-(trimethylammonio)propoxy]ethyl cellulose ether chloride, amphoteric copolymers having a cationic net charge which consist of acrylamidopropyl trimethylammonium chloride and acrylic acid in a molar ratio of 60:40 to 95:5, preferably 75:25 to 90:10, and terpolymers of acrylic acid, diallyldimethylammonium chloride and acrylamide, as well as mixtures of two or three of said polymers.

Particularly preferred polymer B mixtures include 2-[2-hydroxy-3-(trimethylammonio)-propoxy]ethyl cellulose ether chloride and at least one amphoteric copolymer having a cationic net charge which consists of acrylamidopropyl trimethylammonium chloride and acrylic acid in a molar ratio of 60:40 to 95:5, preferably 75:25 to 90:10.

Other particularly preferred polymer B mixtures include 2-[2-hydroxy-3-(trimethylammonio)propoxy]ethyl cellulose ether chloride, at least one amphoteric copolymer having a cationic net charge which consists of acrylamidopropyl trimethylammonium chloride and acrylic acid in a molar ratio of 60:40 to 95:5, preferably 75:25 to 90:10, and at least one terpolymer of acrylic acid, diallyldimethylammonium chloride and acrylamide.

Permanently cationic polymers B which are likewise extremely preferred according to the invention are selected from Polyquaternium-10, amphoteric copolymers having a cationic net charge which consist of acrylamidopropyl trimethylammonium chloride and acrylic acid in a molar ratio of 60:40 to 95:5, preferably 75:25 to 90:10, and Polyquaternium-39, as well as mixtures of two or three of said polymers.

Other particularly preferred polymer B mixtures include Polyquaternium-10 and at least one amphoteric copolymer having a cationic net charge which consists of acrylamidopropyl trimethylammonium chloride and acrylic acid in a molar ratio of 60:40 to 95:5, preferably 75:25 to 90:10.

Other particularly preferred polymer B mixtures include Polyquaternium-10 and at least one amphoteric copolymer having a cationic net charge which consists of acrylamidopropyl trimethylammonium chloride and acrylic acid in a molar ratio of 60:40 to 95:5, preferably 75:25 to 90:10, and Polyquaternium-39.

Preferred coloring agents according to the invention include the at least one permanently cationic polymer B in a total amount of 0.05 to 1.5% by weight, preferably 0.1 to 1.0% by weight, particularly preferably 0.2 to 0.8% by weight, in each case based on the weight of the coloring agent according to the invention.

The coloring preparation according to the invention or used in the method according to the invention preferably includes at least one alkalizing agent, selected from ammonium hydroxide, monoethanolamine and sodium silicates, and mixtures thereof.

In order to achieve the desired long-lasting coloring of the keratin fibers, a coloring agent must have a pH in the range from 6.5 to 11.0, preferably 8 to 10.5, particularly preferably 8.5 to 10, in each case measured at 20° C. At these pH values, the outer keratin fiber layer opens optimally to absorb the oxidation dye precursors, and the desired effect of the peroxide compound added to the developer emulsion is optimally achieved.

Preferred coloring preparations according to the invention or used in the method according to the invention have a pH in the range from 6.5 to 11.0, preferably 8 to 10.5, particularly preferably 8.5 to 10, in each case measured at 20° C.

With preference, ammonia is used in the form of its aqueous solution. Suitable aqueous ammonia solutions may be 10 to 35% strength solutions (calculated in % by weight, 100 g aqueous ammonia solution thus include 10 to 35 g ammonia). Preferably, ammonia is used in the form of a 20 to 30% strength by weight solution, particularly preferably in the form of a 25% strength by weight solution.

In one particularly preferred embodiment, the coloring agent according to the invention is characterized in that it includes ammonium hydroxide in an amount of 0.20 to 2.5% by weight, preferably 0.5 to 2.0% by weight, more preferably 1.0 to 1.5% by weight and particularly preferably 0.31 to 0.8% by weight, based on the total weight of the coloring agent according to the invention.

Preferred coloring agents according to the invention include monoethanolamine in addition to or instead of ammonium hydroxide.

In order to achieve maximum odor masking and in order to optimize the fastness properties, monoethanolamine is included in a total amount of 0.2 to 6.5% by weight, preferably 0.5 to 4.0% by weight, more preferably 0.7 to 2.5% by weight and particularly preferably 0.8 to 1.6% by weight, based on the total weight of the coloring agent according to the invention.

In the context of the present invention, sodium silicates are chemical compounds which are composed of sodium oxide and silicon dioxide and which may occur in various molar ratios (monosilicate, metasilicate and polysilicate). One example of a sodium silicate is the sodium salt of orthosilicic acid having the empirical formula $Na_4SiO_4$, which is also known as sodium orthosilicate.

Other examples of suitable sodium silicates are disodium metasilicate or sodium metasilicate having the empirical formula $Na_2SiO_3$, disodium disilicate having the empirical formula $Na_2Si_2O_5$, or disodium trisilicate having the empirical formula $Na_2Si_3O_7$.

Silicates in amorphous form can be produced by melting together silicon dioxide and alkali metal oxide in molar ratios of between 1:1 and 4:1. The solids thus obtained are dissolved at approximately 150° C. and 5 bar vapor pressure in order to obtain a solution of the sodium silicates in water; these corresponding solutions are alkali water glasses.

"Alkali water glasses" refer to glass-like (amorphous) sodium silicates solidified from a melt, or to aqueous solutions thereof. The term "sodium water glass" is also used. Sodium water glasses are encompassed by the definition of the sodium silicates within this invention.

The molar composition of water glasses is usually 2 to 4 mol $SiO_2$ to 1 mol alkali metal oxide ($Na_2O$).

One example of a preferred sodium silicate is sodium water glass which is in the form of its aqueous solution, has an $Na_2O$ content of 7.5 to 8.8% by weight and an $SiO_2$ content of 25.0 to 28.5% by weight, and which has the CAS No. 1344-09-5 (Chemical Abstracts Number).

Other coloring agents which are preferred according to the invention include at least one sodium silicate in a total amount of 0.1 to 9% by weight, preferably 0.2 to 8% by weight, particularly preferably 1 to 7.5% by weight, in each case based on the total weight of the coloring agent according to the invention.

Other alkalizing agents, such as potassium hydroxide (KOH) and sodium hydroxide (NaOH), may also be included therein, usually in a total amount of 0.05 to 1.5% by weight, preferably 0.1 to 0.6% by weight, in each case based on the total weight of the coloring agent according to the invention.

The coloring preparation according to the invention or used in the method according to the invention optionally includes further auxiliaries and additives. For instance, it has proven to be preferred according to the invention if the coloring preparation includes at least one thickening agent. No limitations exist in principle with regard to this thickening agent. Both organic and entirely inorganic thickening agents can be used.

Where appropriate, an optionally included polymer A or an optionally included polymer B can already act as a thickening agent. The thickening polymers described below can thus optionally fall under the definition for polymer A or polymer B.

According to a first preferred embodiment, the thickening agent is an anionic, synthetic polymer. Preferred anionic groups are the carboxylate group and the sulfonate group.

Examples of anionic monomers from which the polymeric anionic thickening agents may be made are acrylic acid, methacrylic acid, crotonic acid, itaconic acid, maleic acid anhydride and 2-acrylamido-2-methylpropanesulfonic acid. The acid groups may exist entirely or in part as a sodium, potassium, ammonium, or mono- or triethanolammonium salt. Preferred monomers are maleic anhydride and in particular 2-acrylamido-2-methylpropanesulfonic acid and acrylic acid.

Preferred anionic homopolymers are non-crosslinked and crosslinked polyacrylic acids. In this regard, allyl ethers of pentaerythritol, of sucrose and of propylene may be preferred crosslinking agents. Such compounds are commercially available for example under the trade name Carbopol®. Likewise preferred is the homopolymer of 2-acrylamido-2-methylpropanesulfonic acid, which is commercially available for example under the name Rheothik® 11-80.

Within this first embodiment, it may also be preferred to use copolymers of at least one anionic monomer and at least one nonionogenic monomer. With regard to the anionic monomers, reference is made to the substances listed above. Preferred nonionogenic monomers are acrylamide, methacrylamide, acrylic acid esters, methacrylic acid esters, itaconic acid monoesters and diesters, vinylpyrrolidinone, vinyl ethers and vinyl esters.

The anionic acrylic acid and/or methacrylic acid polymers or copolymers are included in the agents according to the invention preferably in an amount of 0.1 to 10% by weight, particularly preferably 1 to 5% by weight, in each case based on the weight of the agent.

Preferred anionic copolymers are for example copolymers of acrylic acid, methacrylic acid, or $C_1$-$C_6$ alkyl esters thereof, such as those marketed under the INCI name Acrylates Copolymers. One preferred commercial product is for example Aculyn®33 from the company Rohm & Haas. Also preferred, however, are copolymers of acrylic acid, methacrylic acid or $C_1$-$C_6$ alkyl esters thereof and the esters of an ethylenically unsaturated acid and an alkoxylated fatty alcohol. Suitable ethylenically unsaturated acids are in particular acrylic acid, methacrylic acid and itaconic acid; suitable alkoxylated fatty alcohols are in particular Steareth-20 or Ceteth-20. Such copolymers are marketed by the company Rohm & Haas under the trade name Aculyn® 22 and by the company National Starch under the trade names Structure® 2001 and Structure® 3001.

Preferred anionic copolymers are also acrylic acid-acrylamide copolymers and in particular polyacrylamide copolymers comprising sulfonic acid group-containing monomers. One particularly preferred anionic copolymer consists of 70 to 55 mol % acrylamide and 30 to 45 mol % 2-acrylamido-2-methylpropanesulfonic acid, the sulfonic acid group being present entirely or in part as a sodium, potassium, ammonium, or mono- or triethanolammonium salt. This copolymer may also be present in crosslinked form, wherein preferably polyolefinically unsaturated compounds such as tetraallyloxyethane, allylsucrose, allylpentaerythritol and methylene bisacrylamide are used as crosslinking agents. Such a polymer is included in the commercial products Sepigel® 305 and Simulgel®600 from the company SEPPIC. The use of these compounds, which besides the polymer component also include a hydrocarbon mixture ($C_{13}$-$C_{14}$ isoparaffin or isohexadecane) and a nonionogenic emulsifier (Laureth-7 or Polysorbate-80), has proven to be particularly advantageous in the context of the teaching according to the invention.

Polymers of maleic anhydride and methyl vinyl ether, in particular those having crosslinkages, are also preferred thickening agents. A maleic acid-methyl vinyl ether copolymer crosslinked with 1,9-decadiene is commercially available under the name Stabileze® QM.

Preferably, the agent according to the invention or used in the method according to the invention may additionally include at least one anionic acrylic acid and/or methacrylic acid polymer or copolymer. Preferred polymers of this type are:

polymers composed for example of at least 10% by weight acrylic acid-low alkyl ester, 25 to 70% by weight methacrylic acid and optionally up to 40% by weight of a further comonomer, mixed polymers composed of 50 to 75% by weight ethyl acrylate, 25 to 35% by weight acrylic acid and 0 to 25% by weight other comonomers. Suitable dispersions of this type are commercially available, for example under the trade name Latekoll® D (BASF), copolymers composed of 50 to 60% by weight ethyl acrylate, 30 to 40% by weight methacrylic acid and 5 to 15% by weight acrylic acid, crosslinked with ethylene glycol dimethacrylate.

According to another embodiment, the thickening agent is a cationic synthetic polymer. Preferred cationic groups are quaternary ammonium groups. In particular, those polymers in which the quaternary ammonium groups are bound via a $C_1$-$C_4$ hydrocarbon group to a polymer main chain constructed from acrylic acid, methacrylic acid or derivatives thereof have proven to be particularly suitable.

Homopolymers of general formula (HP-1),

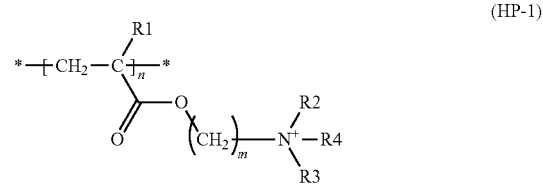

(HP-1)

in which $R^1$=—H or —$CH_3$, R2, R3 and R4 independently of one another are selected from $C_1$-$C_4$ alkyl, alkenyl or hydroxyalkyl groups, m=1, 2, 3 or 4, n is a natural number and $X^-$ is a physiologically acceptable organic or inorganic anion, as well as copolymers consisting substantially of the monomer units shown in formula (HP-1) and nonionogenic monomer units, are particularly preferred cationic polymeric gel formers. Within the scope of these polymers, preference is given according to the invention to those for which at least one of the following conditions applies:

R1 represents a methyl group
R2, R3 and R4 represent methyl groups
m has the value 2.

As physiologically acceptable counter-ions $X^-$, consideration may be given for example to halide ions, sulfate ions, phosphate ions, methosulfate ions and organic ions such as lactate, citrate, tartrate and acetate ions. Halide ions, in particular chloride, are preferred.

One particularly suitable homopolymer is the poly(methacryloxyethyltrimethylammonium) chloride (crosslinked, if desired) having the INCI name Polyquaternium-37. The crosslinking may take place, if desired, with the aid of olefinically polyunsaturated compounds, for example divinylbenzene, tetraallyloxyethane, methylene bisacrylamide, diallyl ether, polyallyl polyglyceryl ether, or allyl ethers of sugars or sugar derivatives such as erythritol, pentaerythritol, arabitol, mannitol, sorbitol, sucrose or glucose. Methylene bisacrylamide is a preferred crosslinking agent.

The homopolymer is preferably used in the form of a nonaqueous polymer dispersion which should have a polymer proportion of not less than 30% by weight. Such polymer dispersions are commercially available under the names Salcare® SC 95 (approximately 50% polymer proportion, further components: mineral oil (INCI name: Mineral Oil) and tridecyl polyoxypropylene polyoxyethylene ether (INCI name: PPG-1-Trideceth-6)) and Salcare® SC 96 (approximately 50% polymer proportion, further components: mixture of diesters of propylene glycol with a mixture of caprylic and capric acid (INCI name: Propylene Glycol Dicaprylate/Dicaprate) and tridecyl polyoxypropylene polyoxyethylene ether (INCI name: PPG-1-Trideceth-6)).

Copolymers comprising monomer units according to formula (HP-1) include as nonionogenic monomer units preferably acrylamide, methacrylamide, acrylic acid $C_1$-$C_4$ alkyl ester and methacrylic acid $C_1$-$C_4$ alkyl ester. Among these nonionogenic monomers, particular preference is given to acrylamide. These copolymers can also be crosslinked as described above in the case of the homopolymers. One copolymer which is preferred according to the invention is the crosslinked acrylamide/methacroyl-oxyethyltrimethylammonium chloride copolymer. Such copolymers, in which the monomers are in a weight ratio of approximately 20:80, are commercially available as an approximately 50% strength nonaqueous polymer dispersion under the name Salcare® SC 92.

In a further preferred embodiment, naturally occurring thickening agents are used. Preferred thickening agents of this embodiment are, for example, nonionic guar gums. Both modified and unmodified guar gums may be used according to the invention. Unmodified guar gums are marketed for example under the trade name Jaguar® C by the company Rhone-Poulenc. Modified guar gums which are preferred according to the invention include $C_1$-$C_6$ hydroxyalkyl groups. The hydroxymethyl, hydroxyethyl, hydroxypropyl and hydroxybutyl groups are preferred. Guar gums modified in this way are known in the prior art and can be produced for example by reacting the guar gums with alkylene oxides. The degree of hydroxyalkylation, which corresponds to the number of alkylene oxide molecules consumed relative to the number of free hydroxyl groups of the guar gums, is preferably between 0.4 and 1.2. Guar gums modified in this way are commercially available under the trade names Jaguar® HP8, Jaguar® HP60, Jaguar® HP120, Jaguar® DC 293 and Jaguar® HP105 from the company Rhone Poulenc.

Further suitable natural thickening agents are also already known from the prior art.

Also preferred according to this embodiment are biosaccharide gums of microbial origin, such as scleroglucan gums or xanthan gums, gums from plant exudates, such as for example gum arabic, ghatti gum, karaya gum, tragacanth gum, carrageenan gum, agar-agar, locust bean flour, pectins, alginates, starch fractions and derivatives such as amylose, amylopectin and dextrins, cellulose derivatives, such as for example methyl cellulose, carboxyalkyl celluloses and hydroxyalkyl celluloses.

Preferred hydroxyalkyl celluloses are in particular the hydroxyethyl celluloses marketed under the names Cellosize® by the company Amerchol and Natrosol® by the company Hercules. Suitable carboxyalkyl celluloses are in particular the carboxymethyl celluloses, such as those marketed under the names Blanose® by the company Aqualon, Aquasorb® and Ambergum® by the company Hercules and Cellgon® by the company Montello.

Preference is also given to starch and derivatives thereof. Starch is a storage substance of plants which occurs primarily in tubers and roots, in cereal seeds and in fruits and can be obtained from a large number of plants in high yield. The polysaccharide, which is insoluble in cold water and forms a colloidal solution in boiling water, can be obtained for example from potatoes, cassava, sweet potato, arrowroot, corn, cereal, rice, legumes such as peas and beans for example, bananas or the marrow of certain types of palm (for example sago palm). According to the invention, use may be made of natural starches obtained from plants and/or of chemically or physically modified starches. Modification can be achieved for example by introducing various functional groups onto one or more of the hydroxyl groups of the starch. These are usually esters, ethers or amides of starch having optionally substituted $C_1$-$C_{40}$ radicals. A corn starch etherified with a 2-hydroxypropyl group is particularly advantageous, such as the one marketed for example by the company National Starch under the trade name Amaze®.

However, nonionic, fully synthetic polymers, such as for example polyvinyl alcohol or polyvinylpyrrolidone, can also be used as thickening agents according to the invention. Preferred nonionic, fully synthetic polymers are marketed for example by the company BASF under the trade name Luviskol®. Besides their excellent thickening properties, such nonionic polymers also enable a significant improvement in the sensory feel of the resulting preparations.

Inorganic thickening agents which have proven to be particularly suitable in the context of the present invention are phyllosilicates (polymeric, crystalline sodium disilicates). Particular preference is given to clays, in particular magnesium aluminum silicates, such as for example bentonite, particularly smectites, such as montmorillonite or hectorite, which may optionally also be suitably modified, and synthetic phyllosilicates, such as for example the magnesium phyllosilicate marketed by the company Süd Chemie under the trade name Optigel®.

In order to further enhance the performance, optionally hydrated $SiO_2$ compound may be added to the composition according to the invention or used in the method according to the invention. It may be preferred according to the invention to use the optionally hydrated $SiO_2$ compounds in amounts of 0.05% by weight to 15% by weight, particularly preferably in amounts of 0.15% by weight to 10% by weight and very particularly preferably in amounts of 0.2% by weight to 5% by weight, in each case based on the composition. The amounts specified indicate in each case the content of the $SiO_2$ compounds (without their water content) in the agents.

With regard to the optionally hydrated $SiO_2$ compounds, the present invention is in principle subject to no limitations. Preference is given to silicic acids, oligomers thereof and polymers thereof, and also salts thereof. Preferred salts are the alkali metal salts, in particular the potassium and sodium salts. The sodium salts are very particularly preferred.

The optionally hydrated $SiO_2$ compounds may be present in different forms. According to the invention, preference is given to using the $SiO_2$ compounds in the form of silica gels, or particularly preferably as water glass. These $SiO_2$ compounds may sometimes be present in aqueous solution.

According to the invention, very particular preference is given to water glasses which are formed from a silicate of formula $(SiO_2)_n(Na_2O)_m(K_2O)_p$, wherein n represents a positive rational number, and m and p independently of one another represent a positive rational number or 0, with the provisos that at least one of the parameters m or p is different from 0 and the ratio between n and the sum of m and p is between 1:4 and 4:1. Preference is given to metasilicates in which the ratio between n and the sum of m and p is 1.2 or below.

Besides the components described by the empirical formula, the water glasses may also include further additives in small amounts, such as for example phosphates or magnesium salts.

Water glasses which are particularly preferred according to the invention are marketed inter alia by the company Henkel under the names Ferrosil® 119, Natronwasserglas 40/42, Portil® A, Portil® AW and Portil® W and by the company Akzo under the name Britesil® C20.

Preferably, an emulsifier or a surfactant is also added to the coloring agents according to the invention or used in the method according to the invention, surface-active substances being referred to as surfactants or emulsifiers depending on the field of application and being selected from anionic, cationic, zwitterionic, amphoteric and non-ionic surfactants and emulsifiers. These substances will be described in detail below.

Suitable anionic surfactants in preparations according to the invention are all anionic surface-active substances suitable for use on the human body. These are characterized by a water-solubilizing, anionic group, such as for example a carboxylate, sulfate, sulfonate or phosphate group, and a lipophilic alkyl group having about 8 to 30 carbon atoms. In addition, glycol or polyglycol ether groups, ester, ether and amide groups and hydroxyl groups may be present in the molecule. Examples of suitable anionic surfactants are, in each case in the form of the sodium, potassium and ammonium and mono-, di- and trialkanolammonium salts having 2 to 4 carbon atoms in the alkanol group,
  linear and branched fatty acids having 8 to 30 carbon atoms (soaps),
  ethercarboxylic acids of formula RO(CH$_2$CH$_2$O)$_x$CH$_2$COOH, in which R is a linear alkyl group having 8 to 30 carbon atoms and x=0 or 1 to 16,
  acyl sarcosides having 8 to 24 carbon atoms in the acyl group,
  acyl taurides having 8 to 24 carbon atoms in the acyl group,
  acyl isethionates having 8 to 24 carbon atoms in the acyl group,
  sulfosuccinic mono- and dialkyl esters having 8 to 24 carbon atoms in the alkyl group and sulfosuccinic monoalkyl polyoxyethyl esters having 8 to 24 carbon atoms in the alkyl group and 1 to 6 oxyethyl groups,
  linear alkanesulfonates having 8 to 24 carbon atoms,
  linear α-olefinsulfonates having 8 to 24 carbon atoms,
  sulfonates of unsaturated fatty acids having 8 to 24 carbon atoms and 1 to 6 double bonds,
  α-sulfo fatty acid methyl esters of fatty acids having 8 to 30 carbon atoms,
  alkyl sulfates and alkyl ether sulfates of formula RO(CH$_2$CH$_2$O)$_x$SO$_3$H, in which R is a preferably linear alkyl group having 8 to 30 carbon atoms and x=0 or 1 to 12,
  mixtures of surface-active hydroxysulfonates,
  sulfated hydroxyalkyl polyethylene and/or hydroxyalkylene propylene glycol ethers,
  esters of tartaric acid and citric acid with alcohols, which constitute addition products of about 2-15 molecules of ethylene oxide and/or propylene oxide onto fatty alcohols having 8 to 22 carbon atoms,
  alkyl and/or alkenyl ether phosphates of formula

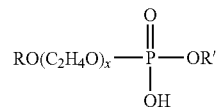

in which R preferably represents an aliphatic, optionally unsaturated hydrocarbon radical having 8 to 30 carbon atoms, R' represents hydrogen, a radical (CH$_2$CH$_2$O)$_y$R and x and y independently of one another represent a number from 1 to 10,
  sulfated fatty acid alkylene glycol esters of formula RC(O)O(alkO)$_n$SO$_3$H, in which R represents a linear or branched, aliphatic, saturated and/or unsaturated alkyl radical having 6 to 22 carbon atoms, alk represents CH$_2$CH$_2$, CHCH$_3$CH$_2$ and/or CH$_2$CHCH$_3$ and n represents a number from 0.5 to 5,
  monoglyceride sulfates and monoglyceride ether sulfates.

Preferred anionic surfactants are alkyl sulfates, alkyl ether sulfates and ethercarboxylic acids having 10 to 18 carbon atoms in the alkyl group and up to 12 glycol ether groups in the molecule.

Zwitterionic surfactants is the term used to refer to those surface-active compounds which carry in the molecule at least one quaternary ammonium group and at least one carboxylate, sulfonate or sulfate group. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. One preferred zwitterionic surfactant is the fatty acid amide derivative known under the INCI name Cocamidopropyl Betaine.

Amphoteric surfactants will be understood to mean those surface-active compounds which, apart from a C$_8$-C$_{24}$ alkyl or acyl group in the molecule, include at least one free amino group and at least one —COOH or —SO$_3$H group and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 24 carbon atoms in the alkyl group. Particularly preferred amphoteric surfactants are N-cocoalkylaminopropionate, cocoacylaminoethylaminopropionate and C$_{12}$-C$_{18}$ acylsarcosine.

It has also proven to be advantageous if the coloring and lightening agents according to the invention include further, nonionogenic surface-active substances. Nonionic surfactants include as the hydrophilic group for example a polyol group, a polyalkylene glycol ether group or a combination of polyol and polyglycol ether group. Such compounds are for example
  addition products of 1 to 50 mol of ethylene oxide and/or 0 to 5 mol of propylene oxide onto linear and branched fatty alcohols having 8 to 30 carbon atoms, such as for example lauryl, myristyl, cetyl, but also stearyl, isostearyl and oleyl alcohol, onto fatty acids having 8 to 30 carbon atoms and onto alkylphenols having 8 to 15 carbon atoms in the alkyl group, addition products, closed at the end group by a methyl or $C_2$-$C_6$ alkyl radical, of 1 to 50 mol of ethylene oxide and/or 0 to 5 mol of propylene oxide onto linear and branched fatty alcohols having 8 to 30 carbon atoms, onto fatty acids having 8 to 30 carbon atoms and onto alkylphenols having 8 to 15 carbon atoms in the alkyl group, such as for example the types available under the trade names Dehydol® LS, Dehydol® LT (Cognis), polyglycerol esters and alkoxylated polyglycerol esters, such as for example poly(3)glycerol diisostearate (commercial product: Lameform® TGI (Henkel)) and poly(2)glycerol polyhydroxystearate (commercial product: Dehymuls® PGPH (Henkel)), polyol fatty acid esters, such as for example the commercial product Hydagen® HSP (Cognis) or Sovermol types (Cognis), higher alkoxylated, preferably propoxylated and in particular ethoxylated, mono-, di- and triglycerides, such as for example glycerol monolaurate+20 ethylene oxide and glycerol monostearate+20 ethylene oxide, amine oxides, hydroxy mixed ethers, sorbitan fatty acid esters and addition products of ethylene oxide onto sorbitan fatty acid esters, such as for example polysorbates and sorbitan monolaurate+20 mol of ethylene oxide (EO), sugar fatty acid esters and addition products of ethylene oxide onto sugar fatty acid esters, addition products of ethylene oxide onto fatty acid alkanolamides and fatty amines, fatty acid N-alkylglucamides, alkylphenols and alkylphenol alkoxylates having 6 to 21, in particular 6 to 15 carbon atoms in the alkyl chain and 1 to 30 ethylene oxide and/or propylene oxide units. Preferred representatives of this class are for example nonylphenol+9 EO and octylphenol+8 EO, alkylpolyglycosides corresponding to general formula RO—$(Z)_x$, where R represents alkyl, Z represents sugar and x represents the number of sugar units. The alkylpolyglycosides which can be used according to the invention may include just one particular alkyl radical R. Usually, however, these compounds are produced from natural fats and oils or mineral oils. In this case, mixtures are present as the alkyl radicals R depending on the starting compounds and/or depending on the respective work-up of said compounds. The alkylpolyglycosides which can be used according to the invention include on average 1.1 to 5 sugar units. Alkylpolyglycosides having x values of 1.1 to 2.0 are preferred. Very particular preference is given to alkylglycosides in which x is 1.1 to 1.8. The alkoxylated homologs of said alkylpolyglycosides can also be used according to the invention. These homologs may include on average up to 10 ethylene oxide and/or propylene oxide units per alkylglycoside unit.

The anionic, nonionic, zwitterionic or amphoteric surfactants are used in amounts of 0.1 to 45% by weight, preferably 1 to 30% by weight and very particularly preferably 1 to 15% by weight, based on the total amount of the ready-to-use agent.

Also preferred according to the invention are cationic surfactants of the quaternary ammonium compound, esterquat and amidoamine type. Preferred quaternary ammonium compounds are ammonium halides, in particular chlorides and bromides, such as alkyl trimethylammonium chlorides, dialkyl dimethylammonium chlorides and trialkyl methylammonium chlorides, for example cetyl trimethylammonium chloride, stearyl trimethylammonium chloride, distearyl dimethylammonium chloride, lauryl dimethylammonium chloride, lauryl dimethylbenzylammonium chloride and tricetyl methylammonium chloride, as well as the imidazolium compounds known under the INCI names Quaternium-27 and Quaternium-83. The long alkyl chains of the aforementioned surfactants preferably have 10 to 18 carbon atoms. Other cationic surfactants which can be used according to the invention are the quaternized protein hydrolysates.

The alkylamidoamines are usually prepared by amidation of natural or synthetic fatty acids and fatty acid fractions with dialkylaminoamines and are characterized by their good biodegradability alongside a good conditioning effect. One compound from this substance group which is particularly suitable according to the invention is the stearamidopropyl dimethylamine available commercially under the name Tegoamid® S 18.

Also highly biodegradable are quaternary ester compounds, so-called "esterquats." Esterquats are known substances which include both at least one ester function and at least one quaternary ammonium group as a structural element. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. Such products are marketed for example under the brand names Stepantex®, Dehyquart® and Armocare®. The products Armocare® VGH-70, an N,N-bis(2-palmitoyloxyethyl)dimethylammonium chloride, as well as Dehyquart® F-75, Dehyquart® C-4046, Dehyquart® L80 and Dehyquart® AU-35 are examples of such esterquats.

The cationic surfactants are included in the agents used according to the invention preferably in amounts of 0.05 to 10% by weight, based on the total agent. Particular preference is given to amounts of 0.1 to 5% by weight.

In one preferred embodiment, preference may be given to nonionic, zwitterionic and/or amphoteric surfactants and mixtures thereof.

In another preferred embodiment, the effect of coloring agents according to the invention or used in the method according to the invention can be enhanced by emulsifiers. Such emulsifiers are for example addition products of 4 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group, $C_{12}$-$C_{22}$ fatty acid monoesters and diesters of addition products of 1 to 30 mol of ethylene oxide onto polyols having 3 to 6 carbon atoms, in particular onto glycerol, ethylene oxide and polyglycerol addition products onto methyl glucoside fatty acid esters, fatty acid alkanolamides and fatty acid glucamides, $C_8$-$C_{22}$ alkyl mono- and oligoglycosides and the ethoxylated analogs thereof, preference being given to degrees of oligomerization of 1.1 to 5, in particular 1.2 to 2.0, and glucose as the sugar component, mixtures of alkyl-(oligo)-glucosides and fatty alcohols, for example the commercially available product Montanov® 68, addition products of 5 to 60 mol of ethylene oxide onto castor oil and hydrogenated castor oil, partial esters of polyols having 3 to 6 carbon atoms with saturated fatty acids having 8 to 22 carbon atoms, sterols, sterols being understood to mean a group of steroids which carry a hydroxyl group on carbon atom 3 of the steroid backbone and are isolated both from animal tissue (zoo sterols) and plant fats (phytosterols). Examples of zoo sterols are cholesterol and lanosterol. Examples of suitable phytosterols are ergosterol, stigmasterol and sitosterol. Sterols, the so-called mycosterols, are also isolated from fungi and yeasts, phospholipids, especially glucose phospholipids, which are obtained for example as lecithins or phosphatidylcholines from for example egg yolk or plant seeds (for example soya beans), fatty acid esters of sugars and sugar alcohols, such as sorbitol, polyglycerols and polyglycerol derivatives, such as for example polyglycerol poly-12-hydroxystearate (commercial product: Dehymuls® PGPH), linear and branched fatty acids having 8 to 30 carbon atoms, and the Na, K, ammonium, Ca, Mg and Zn salts thereof.

The agents according to the invention or used in the method according to the invention include the emulsifiers preferably in amounts of 0.1 to 25% by weight, in particular 0.5 to 15% by weight, based on the total amount of the ready-to-use agent.

According to the invention, particular preference may be given to nonionogenic emulsifiers and surfactants having an HLB value of 10-15. Among these emulsifier types, very particular preference may be given to those emulsifiers which include no ethylene oxide and/or propylene oxide in the molecule.

The agents according to the invention may also include further active substances, auxiliaries and additives, such as for example nonionic polymers, such as for example vinylpyrrolidinone/vinyl acrylate copolymers, polyvinylpyrrolidinone, vinylpyrrolidinone/vinyl acetate copolymers, polyethylene glycols and polysiloxanes;

silicones such as volatile or non-volatile, straight-chain, branched or cyclic, crosslinked or non-crosslinked polyalkylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy and/or hydroxyl groups (dimethicone copolyols), linear polysiloxane (A)/polyoxyalkylene(B) block copolymers, grafted silicone polymers having a non-silicone-containing organic backbone or having a polysiloxane backbone, such as for example the commercial product Abil B 8832 from the company Degussa, which is marketed under the INCI name Bis-PEG/PPG-20/20 Dimethicone, or mixtures thereof;

cationic polymers such as quaternized cellulose ethers, polysiloxanes having quaternary groups, dimethyldiallylammonium chloride polymers, acrylamide/dimethyldiallylammonium chloride copolymers, dimethylaminoethyl methacrylate/vinylpyrrolidinone copolymers quaternized with diethyl sulfate, vinylpyrrolidinone/imidazolinium methochloride copolymers and quaternized polyvinyl alcohol;

zwitterionic and amphoteric polymers, such as for example acrylamidopropyl-trimethylammonium chloride/acrylate copolymers and octylacrylamide/methyl methacrylate/tert-butylaminoethyl methacrylate/2-hydroxypropyl methacrylate co-polymers, diallyldimethylammonium chloride/acrylate copolymers, t-butylaminoethyl methacrylate/N-(1,1,3,3-tetramethylbutyl) acryl-amide/acrylate(/methacrylate) copolymers;

anionic polymers such as for example polyacrylic acids, crosslinked polyacrylic acids, vinyl acetate/crotonic acid copolymers, vinylpyrrolidinone/vinyl acrylate copolymers, vinyl acetate/butyl maleate/isobornyl acrylate copolymers, methyl vinyl ether/maleic anhydride copolymers and acrylic acid/ethyl acrylate/N-t-butylacrylamide terpolymers, further thickening agents such as agar-agar, guar gum, alginates, xanthan gum, gum arabic, karaya gum, locust bean flour, linseed gum, dextrans, cellulose derivatives, for example methyl cellulose, hydroxyalkyl cellulose and carboxymethyl cellulose, starch fractions and derivatives such as amylose, amylopectin and dextrins, clays such as for example bentonite or fully synthetic hydrocolloids such as for example polyvinyl alcohol;

structuring agents such as glucose and lactic acid;

hair-conditioning compounds such as phospholipids, for example soya lecithin, egg lecithin and cephalins as well as silicone oils;

perfume oils, dimethyl isosorbide and cyclodextrins;

solvents and solubilizing agents such as ethanol, isopropanol, ethylene glycol, propylene glycol, glycerol and diethylene glycol;

active substances to improve the fiber structure, in particular mono-, di- and oligosaccharides such as for example glucose, galactose, fructose, fruit sugars and lactose;

quaternized amines such as methyl-1-alkylamidoethyl-2-alkylimidazolinium methosulfate;

defoaming agents such as silicones;

protein hydrolysates of animal and/or plant origin, such as for example elastin, collagen, keratin, silk and lactoprotein protein hydrolysates, or almond, rice, pea, potato and wheat protein hydrolysates, as well as those in the form of their fatty acid condensation products or optionally anionically or cationically modified derivatives thereof;

vegetable oils, for example macadamia nut oil, kukui nut oil, palm oil, amaranth seed oil, peach kernel oil, avocado oil, olive oil, coconut oil, rapeseed oil, sesame oil, jojoba oil, soybean oil, peanut oil, evening primrose oil and tea tree oil;

substances for adjusting the pH, such as for example conventional acids, in particular edible acids and bases;

active substances such as panthenol, pantothenic acid, pantolactone, allantoin, pyrrolidinonecarboxylic acids and salts thereof as well as bisabolol;

polyphenols, in particular hydroxycinnamic acids, 6,7-dihydroxycoumarins, hydroxybenzoic acids, catechins, tannins, leucoanthocyanidins, anthocyanidins, flavanones, flavones and flavonols;

ceramides, preferably the sphingolipids such as ceramide I, ceramide II, ceramide 1, ceramide 2, ceramide 3, ceramide 5 and ceramide 6, or pseudoceramides, such as in particular N—($C_8$-$C_{22}$-Acyl)-($C_8$-$C_{22}$-acyl)-hydroxyproline;

vitamins, provitamins and vitamin precursors, in particular those of groups A, $B_3$, $B_5$, $B_6$, C, E, F and H;

plant extracts such as for example the extracts of aloe vera, *angelica*, anise, apricot, benzoin, bergamot, birch, nettle, calamus, blackcurrant, costus, hibiscus, oak bark, elemi, tarragon, pine needles, *galbanum*, geranium, *ginseng*, grapefruit, guaiac wood, green tea, *hamamelis*, restharrow, hops, coltsfoot, ginger root, iris, jasmine, chamomile, cardamom, clover, burdock root, pine, kiwi fruit, coconut, coriander, caraway, mountain pine, lavender, lemon grass, lily, lime, linden blossom, lychee, mace, malva, almond, mango, lemon balm, melon, meristem, myrrh, neroli, olibanum, opoponax, orange, patchouli, petitgrain, stone pine, wild thyme, rooibos, rose, rosemary, horse chestnut, sandalwood, sage, horsetail, yarrow, celery, spruce, thyme, juniper, vine leaves, hawthorn, wheat, lady's-smock, ylang-ylang, cedar and lemon;

cholesterol;

consistency regulators such as sugar esters, polyol esters or polyol alkyl ethers;

fats and waxes such as spermaceti, beeswax, Montan wax and paraffins;

fatty acid alkanolamides;

swelling and penetration substances such as glycerol, propylene glycol monoethyl ether, carbonates, hydrogencarbonates, guanidines, ureas, and primary, secondary, and tertiary phosphates;

pearlescent agents such as ethylene glycol mono- and distearate as well as PEG-3 distearate;

pigments;

antioxidants.

These further substances will be selected by the person skilled in the art according to the desired properties of the agents.

EXAMPLES

The following color creams were produced (figures given in % by weight):

| Composition | E1 | E2 | E3 | E4 |
|---|---|---|---|---|
| Water, demineralized | ad 100 | | | |
| 1,2-Propanediol | 6.0 | 6.0 | 6.0 | 6.0 |
| Cetearyl Alcohol | 9.0 | 9.0 | 9.0 | 9.0 |
| Ceteareth-20 | 2.4 | 2.4 | 2.4 | 2.4 |
| Sterareth-100 | 0.6 | 0.6 | 0.6 | 0.6 |
| Paraffinum Liquidum | 2.5 | 2.5 | 2.5 | 2.5 |
| Glyceryl Monostearate | 0.5 | 0.5 | 0.5 | 0.5 |
| Anhydrous sodium sulfite | 0.1 | 0.1 | 0.1 | 0.1 |
| EDETA powder | 0.5 | 0.5 | 0.5 | 0.5 |
| Hydrolyzed wheat protein | 0.2 | 0.2 | 0.2 | 0.2 |
| Hydrolyzed silk protein | 0.2 | 0.2 | 0.2 | 0.2 |
| PVP solution 30% | — | 2.0 | 2.0 | 2.0 |
| L-Arginine | 0.2 | 0.2 | 0.2 | 0.2 |
| Lysine HCl | 0.2 | 0.2 | 0.2 | 0.2 |
| Succinic acid disodium salt hexahydrate | 1.5 | 1.5 | 1.5 | 1.5 |
| Maleic acid | — | — | — | 0.2 |
| Vitamin C e 300 DAB | — | 0.05 | 0.05 | 0.05 |
| DC CE-8411 Smooth Plus Emulsion | — | 2.0 | 2.0 | 2.0 |
| Apricot kernel oil | — | 0.2 | 0.2 | 0.2 |
| Ammonia 25% | 12.0 | 12.0 | 12.0 | 12.0 |
| Parfum | 0.5 | 0.5 | 0.5 | 0.5 |
| p-Toluylenediamine sulfate | 0.2 | 0.2 | 0.2 | 0.2 |
| Resorcinol | 0.08 | 0.08 | 0.1 | 0.1 |
| 2-Methylresorcinol | 0.020 | 0.020 | — | — |
| 4-Chlororesorcinol | 0.02 | 0.02 | — | — |
| 2-Amino-3-hydroxypyridine | 0.009 | 0.009 | — | — |
| m-Aminophenol | 0.004 | 0.004 | 0.01 | 0.01 |
| 4-Amino-3-methylphenol | — | — | 0.02 | 0.02 |
| p-Amino-o-cresol | — | — | 0.008 | 0.008 |

| Composition | E5 | E6 | E7 | E8 |
|---|---|---|---|---|
| Water, demineralized | ad 100 | | | |
| Carbomer | 0.1 | 0.1 | 0.1 | 0.1 |
| Ammonia 25% | 12.5 | 12.5 | 12.5 | 12.5 |
| Fatty Alcohol Sulfate-Na C16-18 | 0.8 | 0.8 | 0.8 | 0.8 |
| Sodium Laureth Sulfate 27% | 5.1 | 5.1 | 5.1 | 5.1 |
| Potassium hydroxide 50% | 1.2 | 1.2 | 1.2 | 1.2 |
| Oleic acid | 0.4 | 0.4 | 0.4 | 0.4 |
| EDETA powder | 0.2 | 0.2 | 0.2 | 0.2 |
| Glyceryl Monostearate | 4.6 | 4.6 | 4.6 | 4.62 |
| 2-Octyldodecanol | 2.3 | 2.3 | 2.3 | 2.3 |
| Cetearyl alcohol | 13.9 | 13.9 | 13.9 | 13.9 |
| Ceteareth-20 | 3.5 | 3.5 | 3.5 | 3.5 |
| Anhydrous sodium sulfite | 0.1 | 0.1 | 0.1 | 0.1 |
| PVP solution 30% | 1.5 | 1.5 | — | — |
| L-Arginine | 0.2 | 0.2 | 0.2 | 0.2 |
| Lysine HCl | 0.2 | 0.2 | 0.2 | 0.2 |
| Succinic acid | — | 1.0 | — | — |
| Succinic acid disodium salt hexahydrate | — | — | 1.0 | — |
| Maleic acid | 1.0 | — | 1.0 | 2.0 |
| Vitamin C e 300 DAB | 0.05 | 0.05 | 0.05 | 0.05 |
| Parfum | 0.4 | 0.4 | 0.4 | 0.4 |
| p-Toluylenediamine sulfate | 0.1 | 0.1 | 0.1 | 0.1 |
| Resorcinol | 0.06 | 0.06 | 0.06 | 0.06 |
| 2-Methylresorcinol | 0.003 | 0.003 | 0.003 | 0.003 |
| p-Amino-o-cresol | 0.002 | 0.002 | 0.002 | 0.002 |
| 4-Amino-3-nitrophenol | 0.01 | 0.01 | 0.01 | 0.01 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A coloring agent for keratin fibers, in particular for human hair, including—based on its weight— a) one or more of oxidation dye precursors, substantive dyes and mixtures thereof, b) 0.1 to 5% by weight dicarboxylic acid(s) having 2 to 10 carbon atoms and/or salt(s) of said acid(s), c) 20 to 95% by weight water d) between 0 and 0.1% by weight peroxide compound(s); and e) at least one oligomer of general formula (III) having a molecular weight of 200 to 2000 Dalton

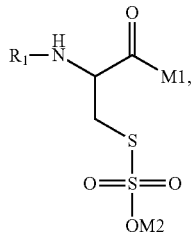

(III)

wherein
R1 represents a hydrogen atom or a structural element of formula (IV)

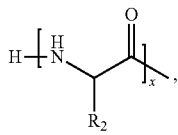

(IV)

wherein
x represents an integer from 1 to 100,
each R2 independently represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group,
M1 represents the group —OM2 or a structural element of formula (V)

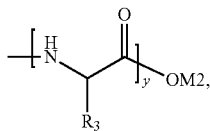

(V)

wherein
y represents an integer from 1 to 100,
each R3 independently represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazol-4-ylmethyl group, a 1H-indol-3-ylmethyl group or a (sulfosulfanyl)methyl group, and
M2 represents a hydrogen atom, an equivalent of a monovalent or polyvalent cation or an ammonium ion $(NH_4)^+$, wherein one or more compounds of the above formula (III) are included in a total amount of 0.001 to 2.5% by weight based on the weight of the coloring agent according to the invention.

2. The coloring agent according to claim 1, including 0.05 to 5% by weight oxidation dye precursors.

3. The coloring agent according to claim 1, including 0.05 to 5% by weight substantive dye(s).

4. The coloring agent according to claim 1, wherein the at least one dicarboxylic acid having 2 to 10 carbon atoms is selected from the group consisting of succinic acid, oxalic acid, malonic acid, adipic acid, pimelic acid, suberic acid, azelaic acid, sebacic acid, maleic acid, fumaric acid and mixtures of said acids.

5. The coloring agent according to claim 1, wherein the at least one dicarboxylic acid having 2 to 10 carbon atoms is included in a total amount of 0.2 to 4% by weight, converted to the undissociated acid and based on the weight of the coloring agent.

6. The coloring agent according to claim 1, including less than 0.005 by weight peroxide compounds.

7. The coloring agent according to claim 1, further including at least one amino acid selected from the group consisting of arginine, lysine, histidine, asparagine, glutamine, cysteine, methionine, tryptophan and mixtures thereof, in a total amount of 0.05 to 3% by weight converted to the undissociated acid and based on the weight of the coloring agent.

8. The coloring agent according to claim 1, wherein one or more compounds of formula (III) are included in a total amount of 0.001 to 2.5% by weight based on the weight of the coloring agent according to the invention.

9. The coloring agent according to claim 1, further including at least one polymer A, which has at least ten constituent units of formula (I)

(I)

in which
X represents nitrogen or oxygen and
$R^1$ and $R^2$ in each case independently of one another represent hydrogen or a C2-C10 acyl group or $R^1$ and $R^2$ together with X form a five-membered or six-membered, saturated or unsaturated ring which optionally includes further heteroatoms selected from N and O and/or is optionally substituted with at least one C1-C6 alkyl group and/or with at least one functional group, and
p=0 when X represents oxygen and p=1 when X represents nitrogen,
the polymer A including no permanently ionic constituent units,
wherein the at least one polymer A having at least ten constituent units of formula (I) is included in a total amount of 0.2 to 5% by weight based on the weight of the coloring agent.

10. A method for the oxidative coloring of keratin fibers, in particular human hair, which comprises:
I. providing a composition (A) that includes the coloring agent according to claim 1,
II. providing a composition (B) that includes at least one peroxide compound, wherein the composition (B) has a pH in the range of 2.5 to 6.5 measured at 20° C.,
III. mixing the compositions (A) and (B) with one another, then immediately
IV. applying the mixture of (A) and (B) to the keratin fibers, and
V. rinsing out after a leave-in time of 0.1 to 60 minutes,
VI. optionally further hair treatments, including styling, conditioning and/or drying.

* * * * *